United States Patent [19]

Barker et al.

[11] 4,192,954

[45] Mar. 11, 1980

[54] PROCESS FOR PREPARING 2,2-BIS(4-HYDROXY-PHENYL) PROPANE FROM DISTILLATION BY-PRODUCTS THEREOF

[75] Inventors: Henry P. Barker, Lock Haven, Pa.; Lawrence C. Mitchell, Mt. Vernon, Ind.

[73] Assignee: General Electric Company, Pittsfield, Mass.

[21] Appl. No.: 863,666

[22] Filed: Dec. 23, 1977

[51] Int. Cl.$^2$ .................. C07C 37/44; C07C 37/24
[52] U.S. Cl. ................................ 568/723; 568/724; 568/728
[58] Field of Search .................. 568/724, 728, 723

[56] References Cited

U.S. PATENT DOCUMENTS

| | | | |
|---|---|---|---|
| 3,073,868 | 1/1963 | Prahl et al. | 568/724 |
| 3,221,061 | 11/1965 | Grover et al. | 568/728 |
| 3,290,390 | 12/1966 | Prahl et al. | 568/728 |
| 3,290,391 | 12/1966 | Prahl et al. | 568/724 |
| 3,326,986 | 6/1967 | Dugan et al. | 568/724 |
| 3,673,262 | 6/1972 | Prahl et al. | 568/724 |
| 3,919,330 | 11/1975 | Kwantes et al. | 568/724 |
| 3,972,950 | 8/1976 | Kwantes | 568/724 |

FOREIGN PATENT DOCUMENTS

| | | |
|---|---|---|
| 1294664 | 5/1969 | Fed. Rep. of Germany . |
| 54374 | 3/1967 | German Democratic Rep. . |
| 66-17478 | 2/1960 | Japan . |
| 1149322 | 4/1969 | United Kingdom . |

OTHER PUBLICATIONS

Hert et al., "C.A.", 67: 53879h, (1967).
Kunoshimo Chemical, Ltd., "C.A.", 66:38331, (1967).

*Primary Examiner*—Norman Morgenstern
*Attorney, Agent, or Firm*—Morgan, Finnegan, Pine, Foley & Lee

[57] ABSTRACT

A process is disclosed for the production of 2,2-bis(4-hydroxyphenyl) propane, herein referred to as bisphenol-A, from by-products remaining after purification distillation of bisphenol-A produced from a condensation reaction of phenol and acetone. The process comprises mixing the by-products with phenol and adding anhydrous hydrogen chloride under superatmospheric pressure to the resulting mixture to isomerize those by-products isomerizable to bisphenol-A for subsequent recovery.

5 Claims, No Drawings

PROCESS FOR PREPARING 2,2-BIS(4-HYDROXY-PHENYL) PROPANE FROM DISTILLATION BY-PRODUCTS THEREOF

This invention concerns a process using anhydrous hydrogen chloride (HCl) under superatmospheric pressure to produce 2,2-bis(4-hydroxyphenyl) propane from by-products remaining after purification distillation of 2,2-bis(4-hydroxyphenyl) propane produced from a condensation reaction of phenol and acetone.

BACKGROUND OF THE INVENTION

The use of high purity 2,2-bis(4-hydroxyphenyl) propane, herein referred to as bisphenol-A, as a reactant in the preparation of subsequent formulations such as in the preparation of polycarbonate resins is well known in the art. One method for obtaining the purity needed of the bisphenol-A is to distill crude bisphenol-A. In such distillations, various by-products remain and these primarily include higher condensation products of bisphenol-A, condensation products of phenol and acetone produced in the original bisphenol-A formation, colored substances, isomers of bisphenol-A, and the like. Prahl et al, U.S. Pat. No. 3,290,390, disclose the addition of phenol to the by-products and contacting this resulting mixture with an acidic agent such as hydrogen chloride at between room temperature and 150° C. to produce therefrom bisphenol-A. However, the method of Prahl et al requires, according to their examples, 16 hours or more reaction time.

It has now been discovered that it is possible to convert such by-products isomerizable to bisphenol-A to said bisphenol-A in a vastly shorter period of time by treating a mixture of the by-products and phenol with anhydrous hydrogen chloride under superatmospheric pressure. The process of this invention yields bisphenol-A in solution for a subsequent recovery such as by cooling the solution to produce a 1:1 bisphenol-A/phenol adduct, from which the bisphenol-A can then be recovered, by procedures known per se.

In practice, commercial plants utilize distillation of bisphenol-A as a step in the purification process. The bottoms from the distillation are called "tars", and conventionally these are disposed of by burning. This represents a serious loss in yield because tars contain from 20–60% bisphenol-A plus the isomerizable by-products mentioned above. Experiments have shown that the amount of bisphenol-A in a typical tar can be more than doubled by isomerization with HCl at 45 psig and more than 70% of this bisphenol-A can be recovered, e.g., by crystallization. The mother liquor from the crystallization can be stripped of phenol (for recycle) in a separate column, and the diminished quantity of "tar" remaining can be burned or otherwise utilized.

DESCRIPTION OF THE INVENTION

According to this invention, there is provided a process for the production of 2,2-bis(4-hydroxyphenyl) propane from by-products which contain products isomerizable to 2,2-bis(4-hydroxyphenyl) propane and which remain after purification distillation of 2,2-bis(4-hydroxyphenyl) propane produced by the condensation of phenol and acetone, said process comprising:

(i) mixing said by-products with phenol;

(ii) adding anhydrous hydrogen chloride under superatmospheric pressure to the resulting mixture and isomerizing said by-products to 2,2-bis(4-hydroxyphenyl) propane; and (iii) subsequently recovering said 2,2-bis(4-hydroxyphenyl) propane.

The by-products are generally referred to as waste streams in commercial procedures for the purification of bisphenol-A, and are many times merely disposed of without treatment to reclaim additional bisphenol-A. In general, the by-products are (1) tar by-products, defined as higher condensation products of bisphenol-A, which are bisphenol-A molecules coupled with themselves and which remain as residue in the purification distillation of bisphenol-A, and (2) isomer by-products, defined as condensation products of phenol and acetone removed with the bisphenol-A fraction during said purification distillation. The by-products further include colored substances and various other unknowns.

Obviously, not all components of these by-products are viable candidates for conversion to bisphenol-A. However, it has now been discovered that within a relatively short period of time, additional bisphenol-A can be claimed from these by-products by mixing said by-products with anhydrous hydrogen chloride under superatmospheric pressure, preferably from about 15 to about 80 psig, and especially preferably about 45 psig. The ratio of phenol to by-product which creates a preferred mixture is about 1–1.5:1 by weight. Preferably, the temperature in step (ii) is from about 30° to about 65° C., and especially preferably from about 45° to about 55° C. The hydrogen chloride must be thoroughly mixed with the phenol and by-product reactants at superatmospheric pressure. While increasing the pressure increases the reaction rate, a pressure of about 45 psig at about 50° C. permits completion of the reaction in 2–3 hours and effectively isomerizes those by-products isomerizable to bisphenol-A. In general, about one-third of the by-products are isomerized to bisphenol-A for subsequent removal.

Recovery of the bisphenol-A thus produced can be performed by various procedures known in the art. One such procedure first strips the hydrogen chloride from the mixture, as known in the art, and then allows the mixture to cool to a temperature where an essentially equimolar adduct of bisphenol-A/phenol crystallizes. Said adduct can be mechanically removed such as by filtration or centrifugation from the remaining components and the bisphenol-A separated therefrom.

DESCRIPTION OF THE PREFERRED EMBODIMENTS

The following examples are set forth to illustrate more clearly the principle and practice of this invention to those skilled in the art. Unless otherwise specified, when parts or percents are mentioned, they are parts of percents by weight.

EXAMPLE 1

One thousand grams of phenol and 1000 grams of tar by-products from a phenol-acetone condensation reaction are charged to a 4.16 liter poly(tetrafluoroethylene)-lined reactor to produce a feed having 12.2% bisphenol-A. The reactor has a gas-inlet valve, vent valve, safety-release valve, mechanical stirrer, pressure gauge and temperature gauge. The reactor is evacuated and pressurized with dry HCl to 45 psig (pounds per square inch guage), and said pressure is maintained with the dry HCl. The temperature is maintained at 48°–52° C. throughout the reaction time and the reaction mixture is continuously stirred. At the end of two hours, venting of the HCl is started, with said venting finished in 30 minutes. Analysis by gas chromatography of the completed reaction mix for bisphenol-A content shows 29.5% bisphenol-A in the mix, 2.42 times the amount of the bisphenol-A present in the feed.

The contents of the reactor are distilled to remove HCl and then allowed to cool to 35° C. for formation of a 1:1 bisphenol-A/phenol molar adduct. Results of gas chromatographic analysis of the adduct show 76.4% of the bisphenol-A present in the completed reaction mix is present in the adduct formed.

EXAMPLES 2 TO 10

In like manner, Examples 2 to 10, tabulated in Table I, below, are performed. Example 2 is included to illustrate the comparatively long time period of 8 hours required for adequate yield when a pressure of only 15 psig is employed. Examples 2, 3, 7 and 10 react tar by-products with phenol; Examples 4, 6, 8 and 9 react tar by-products and isomer by-products with phenol; and Example 5 reacts isomer by-products with phenol.

products and phenol is added to a glass-lined mixing tank having a nitrogen atmosphere. A gear pump is employed to then move the mixture to a reaction chamber wherein anhydrous HCl is continuously sparged radially into the chamber at a rate which maintains desired pressure within the chamber and at a location which sparges the HCl into the entering reaction mix to assure adequate mixing of the HCl with the reactants. The reaction chamber used in Examples 11-23 is a 3" diameter polypropylene-lined pipe positioned vertically and having a volume of 5,100 c.c. Both the mixture and the HCl enter the reaction chamber from the bottom. While mixing of HCl and reactants posed no problem in this size chamber and the addition of a static mixer in Examples 21-23 showed no advantage, a larger reaction chamber should be fitted with static mixing apparatus to assure adequate HCl-reactant mixing.

After reacting the mixture for the designated time, the reactants are allowed to leave the reaction chamber under pressure and be collected in a collection chamber from which the HCl is vented and the products then treated as described for Examples 1-10.

The results of Examples 11-23 are tabulated in Table

TABLE I

| Example No. | Ratio Phenol/Tar By-Products/ Isomer By-Products | Reaction Time (Hours) | % Bisphenol-A in Feed | % Bisphenol-A In Completed Reaction Mix | Magnitude of Increase of Bisphenol-A in Product Over Feed | % Bisphenol-A of Completed Reaction Mix Present in Adduct |
|---|---|---|---|---|---|---|
| 2* | 1.0/1.0/0 | 8.0 | 20.2 | 35.0 | 1.74 | 86.1** |
| 3 | 1.5/1.0/0 | 3.0 | 8.7 | 23.4 | 2.68 | 74.4** |
| 4 | 1.5/1.0/0.5 | 2.0 | 12.0 | 20.1 | 1.68 | 53.2 |
| 5 | 1.0/0/1.0 | 2.0 | 15.3 | 19.1 | 1.25 | 71.6 |
| 6 | 1.0/.67/.33 | 2.0 | 11.3 | 19.7 | 1.74 | 69.8 |
| 7 | 1.5/1.0/0 | 2.0 | 8.4 | 15.8 | 1.84 | 53.0** |
| 8 | 2.0/1.0/0.5 | 2.0 | 10.8 | 16.1 | 1.49 | 71.9 |
| 9 | 2.0/1.0/0.5 | 3.0 | 12.9 | 25.5 | 1.82 | 54.7 |
| 10 | 1.33/1.0/0 | 3.0 | 12.7 | 25.2 | 1.98 | 60.1 |

*Pressure: 15 psig; others at 45 psig.
**Crystallization Temperature = 35° C. All others at 30° C.

Examples 1-10 show a magnitude increase of yield of bisphenol-A of from 1.25 times the feed amount of bisphenol-A where only isomers are treated (Example 5) to 2.68 times the feed amount where tar by-products are treated (Example 3) in a period of only 2-3 hours.

EXAMPLES 11-23

While the above Examples exemplify batch reactions, Examples 11-23 exemplify results obtained in a continuous reactor system. In this system, a mixture of tar by- II, below. In each example, the temperature is generally maintained at 50°-60° C. Example 22 is included to illustrate the results obtained when a pressure of 15 psig is employed with a 2 hour residence time. As shown, the completed reaction mixture contains only 1.25 times the quantity of bisphenol-A present in the feed as compared to the average among Examples 11-16, 19, 21 and 23 (all 45-50 psig) of 1.84, or as compared to the overall average including Examples 17, 18, 20 (75-80 psig) as well as Examples 11-16, 19, 21 and 23 of 1.92.

TABLE II

| Example No. | Residence Time (Hours) | HCl Pressure Psig | % Bisphenol-A in Feed | Bisphenol-A Completed Reaction Mix | Magnitude of Increase of Bisphenol-A in Product over Feed |
|---|---|---|---|---|---|
| 11 | 2 | 45-50 | 24.3 | 31.3 | 1.28 |
| 12 | 2 | 45-50 | 21.2 | 31.6 | 1.49 |
| 13 | 2 | 45 | 11.5 | 28.2 | 2.46 |
| 14 | 2 | 50 | 12.3 | 23.9 | 1.94 |
| 15 | 2 | 50 | 9.9 | 20.2 | 2.04 |
| 16 | 3 | 45-50 | 12.5 | 25.4 | 2.03 |
| 17 | 1 | 75-80 | 13.2 | 23.1 | 1.75 |
| 18 | 1½ | 75-80 | 12.5 | 25.6 | 2.05 |
| 19 | 1½ | 45-50 | 12.2 | 26.0 | 2.13 |
| 20 | 1½ | 75-80 | 8.1 | 21.8 | 2.69 |
| 21* | 2 | 45-50 | 17.1 | 28.5 | 1.66 |
| 22*,** | 2 | 15 | 19.7 | 24.7 | 1.25 |

TABLE II-continued

| Example No. | Residence Time (Hours) | HCl Pressure Psig | % Bisphenol-A in Feed | Bisphenol-A Completed Reaction Mix | Magnitude of Increase of Bisphenol-A in Product over Feed |
|---|---|---|---|---|---|
| 23*,** | 2 | 45–50 | 16.6 | 25.5 | 1.54 |

*Koch Engineering Co. Type AY Static Mixer used.
**Isomer by-products added at 0.5/1.0 isomer by-product/tar by-product.

Obviously, other modifications and variations of the present invention are possible in light of the above teachings. It is, therefore, to be understood that changes may be made in the particular embodiments of the invention described which are within the full intended scope of the invention as defined by the appended claims.

We claim:

1. A process for the production of 2,2-bis(4-hydroxyphenyl) propane from by-products which contain products isomerizable to 2,2-bis(4-hydroxyphenyl) propane and which remain after purification distillation of 2,2-bis(4-hydroxyphenyl) propane produced by the condensation of phenol and acetone, said process comprising:
   (i) mixing said by-products with phenol;
   (ii) adding anhydrous hydrogen chloride under superatmospheric pressure to the resulting mixture and isomerizing said by-products to 2,2-bis(4-hydroxyphenyl) propane; and
   (iii) subsequently recovering said 2,2-bis(4-hydroxyphenyl) propane.

2. A process as defined in claim 1 wherein the by-products are higher condensation products of bisphenol-A.

3. A process as defined in claim 1 wherein the by-products are condensation products of phenol and acetone.

4. A process as defined in claim 1 wherein the by-products and phenol in the mixture are essentially equal in weight.

5. A process as defined in claim 1 wherein the superatmospheric pressure in step (ii) is from about 15 to about 80 psig.

* * * * *

UNITED STATES PATENT AND TRADEMARK OFFICE
CERTIFICATE OF CORRECTION

PATENT NO. : U.S. 4,192,954

DATED : March 11, 1980

INVENTOR(S) : Henry Paul Barker & Lawrence Craig Mitchell

It is certified that error appears in the above-identified patent and that said Letters Patent are hereby corrected as shown below:

Col. 2, line 54, "of" should read --or--;
and
Cols. 4 and 6, in fifth heading in TABLE II, both occurrences, --%-- should be inserted before "Bisphenol-A Completed Reaction Mix".

Signed and Sealed this

Twenty-third Day of December 1980

[SEAL]

Attest:

SIDNEY A. DIAMOND

Attesting Officer

Commissioner of Patents and Trademarks